US005611792A

United States Patent [19]

Gustafsson

[11] Patent Number: 5,611,792

[45] Date of Patent: Mar. 18, 1997

[54] VALUE DEVICE FOR ASEPTIC INJECTION AND REMOVAL OF A MEDICAL FLUID INTO/FROM A CONTAINER

[75] Inventor: Sven Gustafsson, Värmdö , Sweden

[73] Assignee: Dicamed AB, Sollentuna, Sweden

[21] Appl. No.: 446,854

[22] PCT Filed: Nov. 30, 1993

[86] PCT No.: PCT/SE93/01031

§ 371 Date: Jul. 21, 1995

§ 102(e) Date: Jul. 21, 1995

[87] PCT Pub. No.: WO94/13247

PCT Pub. Date: Jun. 23, 1994

[30] Foreign Application Priority Data

Apr. 12, 1992 [SE] Sweden .................................. 9203659

[51] Int. Cl.⁶ ...................................................... A61M 5/00

[52] U.S. Cl. .......................... 604/403; 604/411; 604/415; 604/905; 604/86; 604/167; 215/247

[58] Field of Search .................................... 604/403, 408, 604/409, 411, 414, 415, 905, 86, 88, 167, 244; 623/8; 383/3, 43–44; 215/247, 249, 303

[56] References Cited

U.S. PATENT DOCUMENTS

| | | | |
|---|---|---|---|
| 2,783,908 | 3/1957 | Winfield | 215/247 |
| 2,856,929 | 10/1958 | Gossett et al. | 383/3 |
| 3,554,256 | 1/1971 | Anderson | 604/408 |
| 4,632,673 | 12/1986 | Tiitola et al. | 604/415 |
| 4,698,061 | 10/1987 | Makaryk et al. | 604/408 |
| 4,863,453 | 9/1989 | Berger et al. | 604/415 |

FOREIGN PATENT DOCUMENTS

| | | | |
|---|---|---|---|
| 0264044A2 | 4/1988 | European Pat. Off. . | |
| 0503330A1 | 9/1992 | European Pat. Off. . | |
| 2518245 | 11/1975 | Germany . | |
| 1579065 | 11/1980 | United Kingdom | 604/408 |
| WO82/03776 | 11/1982 | WIPO . | |
| WO84/00025 | 1/1984 | WIPO . | |

*Primary Examiner*—John G. Weiss
*Assistant Examiner*—Bruce E. Snow
*Attorney, Agent, or Firm*—Burns, Doane, Swecker & Mathis, LLP

[57] ABSTRACT

A valve device to enable aseptic injection and withdrawal of medical fluids into/from an infusion container. The valve device comprises a valve body with self-sealing passage portion (2), a surrounding portion (3) and a peripheral portion (4), and has an adhesive application surface (5). Located at the underside of the passage portion is a pressure relief zone (6), and at the upper side an insert zone (7). The surrounding portion (3) has a pronounced upright edge. The valve device is manufactured in one piece of the same material and can be simply applied and handled on the occasion of use while retaining aseptic conditions even by persons of impaired sight.

8 Claims, 1 Drawing Sheet

VALUE DEVICE FOR ASEPTIC INJECTION AND REMOVAL OF A MEDICAL FLUID INTO/FROM A CONTAINER

The present invention relates to a valve device for enabling the aseptic injection and withdrawal of medical fluids into/from an infusion container. More particularly, the invention relates to a valve device which comprises a valve body having a centrally located, self-sealing passage portion, a portion surrounding the passage portion and a surrounding peripheral portion. An application surface of the valve device is at least in part adhesive to enable its application onto the infusion container, preferably after the container has been filled. The invention may also find utility in other fields of application where aseptic technique is employed, for example within the food and beverage industry.

During various types of medical infusions, additions of various sorts may be necessary as may certain withdrawals, for example, samples for analysis. These may be exemplified by mineral or vitamin solutions, insulin and the like which are to be supplied to the infusion fluid.

In the case of patients suffering from renal insufficiencies and dependent on dialysis treatment, withdrawals of dialysis fluid via a catheter are necessary, these withdrawals being effected by the actual patient taking a gravity drawn sample via an implanted conduit into a special sample pouch which is sent off, as a unit, for analysis. This is a bulky and impractical, as well as a delicate, routine. Dialysis patients themselves also make additions to the dialysis fluid, as treatment is largely attended to by the patient in the home environment nowadays.

The infusion container is most commonly fitted at the manufacture stage with a stub located alongside the usual outlet. Such containers are manufactured, for example, by Fresenius AG, Bad Homburg. These include a valve construction which is assembled from several parts. Additions and withdrawals are made through the membrane with a syringe.

International Patent Application No. WO 84/00025 describes the use of an injection port having a construction similar to the abovementioned stub, for injecting fluids into an infusion container with a syringe. The port comprises a pad-like membrane included in a complicated and very intricate construction, which results in high manufacturing costs.

During the use of membrane devices of this sort there is always the risk that, due to the pressure the fluid exerts on the membrane, some of the contents of the container are withdrawn with the needle when the needle is taken out through the membrane after the routine, and are then deposited on the surface of the membrane. This involves a clear risk of infection of the contents of the container in those cases where repeated injections and/or withdrawals are necessary. The membrane diameter of the above device is so small that the membrane can be difficult to locate, particularly for a patient whose sight is impaired, which is often the case in renal insufficiency. As sterility is crucial in such treatments, unnecessary probing for the right injection point in these cases involves a not insubstantial infection risk and accordingly jeopardises the patient's health.

Manufacture of infusion containers fitted with the currently employed stubs or injection ports as in WO 84/00025 represents completely unnecessary expense in certain cases as the stubs/ports are not always utilized. Additionally, the attachment of these studs or injection ports to the container is a leakage risk and furthermore constitutes a resource demanding step in an otherwise relatively simple manufacturing process.

International Patent Application WO 82/03776 describes the use of a self-adhesive valve device for the addition or withdrawal of fluid to or from a fluid-filled container. One embodiment with this construction involves a substantial risk of infection because, in this case as well, fluid from the container is easily drawn along through the valve device when the needle is withdrawn after addition/withdrawal. The contents of the container exert a pressure at the injection point which may cause partial loosening of the adhesive device and leakage to arise. This is not desirable as it involves the risk of infection of the contents of the pouch and in the long run can cause dislodgement of the whole valve device. Additionally, this embodiment is difficult to manually grip with the fingers, which makes aseptic application by touch more difficult, while the aseptic insertion of a syringe needle without touching the application surface is also nearly impossible. The consequence of these complications is even more serious if the user is a patient whose sight is impaired.

The object of the present invention is to provide a valve device, primarily for use with infusion containers, which ameliorates the abovedescribed handling and manufacturing drawbacks and enables lower costs and reduced risk of leakage and infection during injection and sample taking.

This object is attained in a valve device of the type described in the introduction, which is characterized in that the underside of the passage portion is defined by a pressure relieving zone provided by an elevation from the application surface, the upper side of the passage portion is defined by an insert zone in the upper side of the valve body provided by a depression in the upper side of the valve body, the surrounding portion of the valve body having a pronounced, substantially sheer upright edge relative to the peripheral portion, and the entire valve device comprising the valve body with the aperture, surrounding and peripheral portions is manufactured in one piece and of the same material.

By providing a safety zone defined by the portion surrounding the passage portion, the risk of touching the insert zone during injection or withdrawal is substantially eliminated while leaving it accessible to the injecting instrument.

The valve device of the invention is contained, prior to use, in a sterile package and is fitted with protective film on the application surface as well as the upper side. The film on the application surface protects a storage-stable adhesive layer, which preferably consists of a storage-stable glue, for subsequent attachment to the sterile-packed infusion container, while the film on the upper side maintains the sterility of the valve body. These films present sections projecting distinctly beyond the edges of the attaching surfaces and may therefore be simply removed, respectively upon application, and upon injection and withdrawal.

The invention will now be described in further detail via a preferred embodiment and with reference to the drawings, in which.

Figure 3:
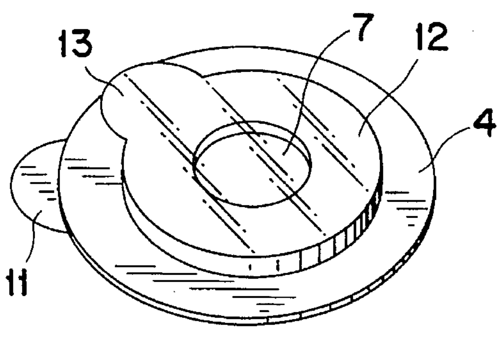
Figure 4:
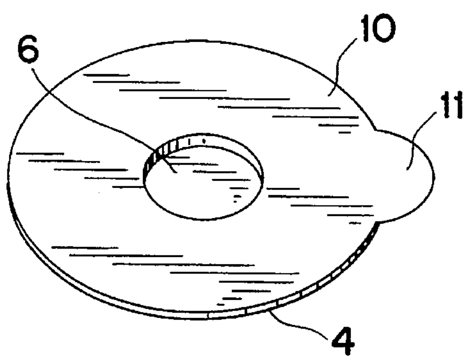

FIG. 3 is a view of the valve device in the earlier figures depicted in perspective obliquely from above, where the insert zone is clearly shown and the films are attached to the respective surfaces, and FIG. 4 is a view of the valve device of the earlier figures shown in perspective obliquely from below, where the pressure relief zone is clearly shown and the lower film adjoins the application surface.

Figure 1:
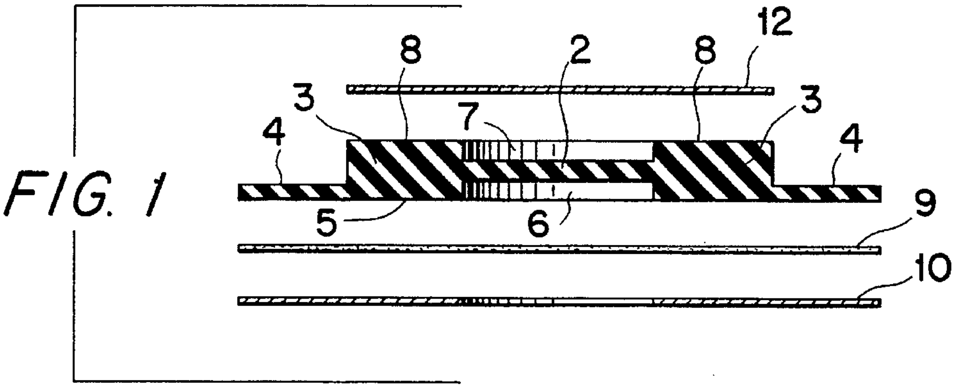
FIG. 1 shows a sectional view which schematically illustrates the fundamental construction of a valve device in accordance with the invention. The respective protective films and adhesive layer are depicted separated from the valve device.

The valve device of the invention depicted in FIG. 1 has a passage portion 2 whose underside is defined by a pressure relief zone 6, which is provided by an elevation from the application surface 5 of the valve device. When the valve device is applied, for example to an infusion container, and an injection needle is inserted through the passage portion 2 and then withdrawn, the pressure relief zone 6 brings about a distribution of the fluid pressure from the punctured container over a larger area, whereby the material in the passage portion can seal sufficiently tightly against the injection needle so that no fluid follows upon withdrawal of the needle. In this way, the risk of infection during repeated use is avoided in an effective fashion. At the same time, the risk of leakage paths between the application surface 5 and the surface of the infusion container is reduced.

The passage portion 2 of the valve device of the invention has an upper surface defined by the insert zone 7, which is provided by a depression in the upper side of the valve body. The depression means that it is easier to find a suitable point for inserting the needle without touching the passage portion, which may thus, with the present invention, be simply executed even by a person with the impaired vision which renal insufficiency, inter alia, often bring about.

The surrounding portion 3 of the valve device shown in FIGS. 1 & 3 has a pronounced, substantially sheer, upright and proportionately high edge relative to the peripheral portion 4, which makes the valve device easy-to-grip and its various parts easy to localize and identify by touch, whereby the valve device is easier to handle than the abovedescribed prior art valve constructions, even for a person whose sight is impaired.

Figure 2:
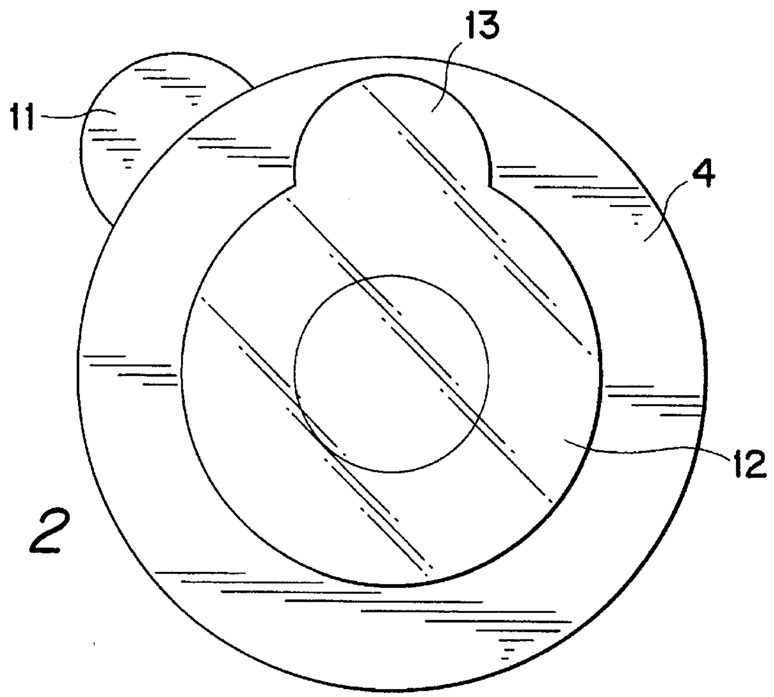
FIG. 2 is a view of the valve device of FIG. 1 from above, where the sections of the film which project distinctly beyond the attaching surfaces are depicted.

The valve device of the present invention is further characterized in that the safety zone 8 defined by the surrounding portion 3, as is most clearly evident in FIGS. 2 & 3, is of a breadth such that the insert zone 7 remains substantially free during injection or withdrawal while it is also accessible to the needle. Accordingly, a certain amount of probing after a suitable injection site with the injection needle may be accepted without risk of contact with those portions which were touched during application. This is of great significance because contact between the patient's hands and the insert zone may be a source of infection. The safety zone 8 must therefore in all essential respects effectively separate the peripheral portion 4, the part which the patient manually presses with the fingers against the container during application, from the passage portion 2 to such an extent that aseptic conditions are maintained during application. At the same time, it is of a breadth such that contact between the fingers and the passage zone is avoided when the valve device is gripped by the upright edges.

FIG. 1 depicts an adhesive layer 9 for applying the valve device to a container, which preferably already contains fluid, the adhesive layer completely or in part covering the application surface 5 of the valve device and adhering to the container. FIG. 4 depicts how this adhesive, up to and including the time of application, is protected by the film 10 which, by virtue of the section 11 distinctly projecting beyond the application surface, is easy to find and remove. The film 10 preferably covers the whole application surface, but leaves the pressure relief zone free in order to avoid contact between the underside of the passage portion and the adhesive layer. The adhesive is preferably an acrylate-based adhesive which tolerates extended storage without deterioration of its adhesive properties.

FIGS. 2 & 3 indicate how the upper side of the valve body, until the occasion of use, is covered with the film 12, which protects both the safety zone 8 and the insert zone 7 from contamination during application. Prior to insertion of a sterile syringe tip or similar into the entry zone, this film is simply removed with the section 13 projecting distinctly beyond the valve body, whereby the sterility of the insert zone is maintained right up to the moment of insertion. This construction was also specifically created bearing in mind users with impaired sight.

The valve device of the invention is manufactured by moulding in one piece, after which follows curing by crosslinking. Leakages which can arise in the joints between assembled parts of the abovedescribed prior art valve devices are avoided by virtue of this homogenous form.

The material from which the valve device of the invention is manufactured is a type of self-sealing elastomer, preferably a natural rubber material. The material should have sufficient flexibility that the valve device as a whole conforms well with respect to an infusion container manufactured of a similarly flexible material, thereby ensuring that the application surface adheres with a tight seal.

One embodiment of the valve device of the invention has the following dimensions: the radius of the entire valve device is 60 mm, the breadth of the peripheral portion 4 is 10 mm, the breadth of the safety zone 8 is 11 mm, the diameter of the passage portion 2 is 18 mm and the height of the valve body is 5 mm.

In that the valve device of the present invention is applied to the container in connection with respective additions and withdrawals, the current need is avoided for every container to be fitted at the manufacturing stage with a stub for a corresponding function. Because it is not always necessary to make either additions or withdrawals in every case in which an infusion container is used, this results in considerable savings in cost.

I claim:

1. A valve device to enable aseptic injection and withdrawal of medical fluids into/from an infusion container, the valve device comprising:

a valve body having a centrally located, self-sealing passage portion, a surrounding portion surrounding the passage portion, and a surrounding peripheral portion surrounding the surrounding portion, the valve device having, on one side thereof, an application surface having an adhesive layer on at least a portion thereof for applying the application surface to an infusion container;

an underside of the passage portion being defined by a pressure relief zone recessed relative to the application surface;

an upper side of the passage portion disposed on an upper side of the valve body, opposite the application surface, being defined by an insert zone recessed relative to at least part of the upper side of the valve body;

the surrounding portion having an edge substantially perpendicular relative to the peripheral portion;

the passage portion, the surrounding portion, and peripheral portion being a one piece structure and being formed from the same material; and a first protective film on the application surface, and a second protective film on the upper side of the valve body, the first protective film protecting the adhesive layer, the second protective film extending at least over the upper side of the passage portion and onto the surrounding portion, the first and second protective films including projecting portions projecting beyond edges of the application surface and the surrounding portion, respectively, for removal of the first and second protective films.

2. A valve device according to claim 1, wherein a portion of the surrounding portion on the upper side of the valve body includes a flat surface for keeping the insert zone free from being touched and for permitting access to the insert zone during injection or withdrawal.

3. A valve device according to claim 2, wherein the valve body is manufactured by molding in one piece from a single material, followed by curing by cross-linking.

4. A valve device according to claim 1, wherein the valve body is manufactured by molding in one piece from a single material, followed by curing by cross-linking.

5. A valve device according to claim 2, wherein the valve body is manufactured from a flexible, self-sealing elastomer, which is conformable with respect to an infusion container formed of a flexible material.

6. A valve device according to claim 1, wherein the valve body is manufactured from a flexible, self-sealing elastomer, which is conformable with respect to an infusion container formed of a flexible material.

7. A valve device according to claim 1, wherein the valve body is manufactured by molding in one piece from a single material, followed by curing by cross-linking.

8. A valve device to enable aseptic injection and withdrawal of medical fluids into/from an infusion container, the valve device comprising:

a valve body having a centrally located, self-sealing passage portion, a surrounding portion surrounding the passage portion, and a surrounding peripheral portion surrounding the surrounding portion, the valve device having, on one side thereof, an application surface having an adhesive layer on at least a portion thereof for applying the application surface to an infusion container;

an underside of the passage portion being defined by a pressure relief zone recessed relative to the application surface;

an upper side of the passage portion disposed on an upper side of the valve body, opposite the application surface, being defined by an insert zone recessed relative to at least part of the upper side of the valve body;

the surrounding portion having an edge substantially perpendicular relative to the peripheral portion; and the passage portion, the surrounding portion, and peripheral portion being a one piece structure and being formed from the same material, wherein the valve body is manufactured from a flexible, self-sealing elastomer, which is conformable with respect to an infusion container formed of a flexible material, and wherein the valve body is manufactured by molding in one piece from a single material, followed by curing by cross-linking.

* * * * *